United States Patent
Hanson (10) Patent No.: US 8,011,238 B2
(45) Date of Patent: Sep. 6, 2011

(54) METHOD FOR CORRECTING THE MEASURED CONCENTRATIONS OF GAS COMPONENTS IN DRILLING MUD

(75) Inventor: Scott A. Hanson, Cypress, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 544 days.

(21) Appl. No.: 12/248,620

(22) Filed: Oct. 9, 2008

(65) Prior Publication Data

US 2010/0089120 A1   Apr. 15, 2010

(51) Int. Cl.
*E21B 49/00* (2006.01)
*G01N 33/24* (2006.01)

(52) U.S. Cl. ............ 73/152.04; 73/19.09; 702/9
(58) Field of Classification Search ........... 73/19.02, 73/19.09, 152.04, 152.18, 152.19; 702/6, 702/9
See application file for complete search history.

(56) References Cited

U.S. PATENT DOCUMENTS

| | | | |
|---|---|---|---|
| 4,492,862 A | | 1/1985 | Grynberg et al. |
| 4,565,086 A | * | 1/1986 | Orr, Jr. ............ 73/19.09 |
| 4,635,735 A | | 1/1987 | Crownover |
| 4,765,182 A | | 8/1988 | Boone |
| 4,887,464 A | | 12/1989 | Tannenbaum et al. |
| 5,199,509 A | | 4/1993 | Hanson |
| 5,447,052 A | | 9/1995 | Hanson |
| 5,648,603 A | | 7/1997 | Hanson |
| 5,939,717 A | | 8/1999 | Mullins |
| 6,290,000 B1 | * | 9/2001 | Zamfes ............ 175/50 |
| 6,974,705 B1 | * | 12/2005 | Brumboiu et al. ...... 436/181 |
| 7,561,997 B1 | * | 7/2009 | Miller ............ 703/10 |
| 7,680,600 B2 | * | 3/2010 | Carnegie et al. ...... 702/17 |
| 7,844,400 B1 | * | 11/2010 | Selman et al. ...... 702/6 |
| 2003/0062472 A1 | | 4/2003 | Mullins et al. |
| 2005/0216196 A1 | * | 9/2005 | Akkurt et al. ...... 702/6 |
| 2007/0159625 A1 | | 7/2007 | DiFoggio |
| 2009/0030614 A1 | * | 1/2009 | Carnegie et al. ...... 702/6 |

OTHER PUBLICATIONS

PCT International Search Report PCT/US 2009/059192—Dated: Oct. 9, 2008.
Wright, Alan C., 1996 Estimation of gas/oil ratios and detection of unusual formation fluids from mud logging gas data, SPWLA 37th Annual Logging Symposium, Jun. 16-19, 1996.

* cited by examiner

*Primary Examiner* — John Fitzgerald
(74) *Attorney, Agent, or Firm* — Carlos L. Hanze (57) ABSTRACT

A method of characterizing formation fluid present in a subsurface earth formation during drilling using methods for correcting the measured concentrations of gas components in drilling mud. Gas trap values for the gas components of interest, light hydrocarbons, are measured during mud logging and are corrected using relative response factors, determined from laboratory fluid analysis values and relative extraction efficiency values. The relative response factors for each gas component of interest can be used for correcting additional gas trap values measured in the same well or for correcting gas trap values measured in surrounding wells utilizing a similar drilling fluid. The corrected gas trap values for each of the gas components of interest can be utilized to calculate gas/oil ratios for characterizing the formation fluid from the volume of drilling mud.

15 Claims, 5 Drawing Sheets

METHOD FOR CORRECTING THE MEASURED CONCENTRATIONS OF GAS COMPONENTS IN DRILLING MUD

FIELD OF THE INVENTION

The present invention relates generally to characterizing formation fluid present in a subsurface earth formation during drilling and more particularly to methods for correcting the measured concentrations of gas components in drilling mud.

BACKGROUND OF THE INVENTION

In oil or gas well drilling operations, drilling fluid (or "mud") is continuously circulated through the inside of the drill pipe and out the drill bit then back up to the surface. Drilling mud is typically made up of clays, chemical additives and an oil or water base. This fluid has several purposes: 1) controlling formation pressure; 2) cleaning the well bore of formation debris; 3) lubricating, cooling, and cleaning the drill bit and drill string; 4) stabilizing the well bore; and 5) limiting the loss of drilling mud to the subsurface formation.

In cleaning the well bore, the circulating drilling mud removes the drill cuttings as well as formation fluid trapped in the pore space or fractures of the rock. During the drilling operation, the entrapped formation fluid and gases in the drilling mud are monitored in real-time at the surface. The recording of the measurements is called mud logging. Mud logging measurements can include temperature, pH, drill rate, chlorides, total hydrocarbon content, and the concentration of specific formation gas components. These logs are important as they enable the drilling operator to ascertain the presence of oil or gas in the formation being drilled. Significant measured gas increases in the drilling mud during drilling indicate oil or gas bearing zones in the formation and are known as "shows".

To measure the amount of formation gas entrapped in the drilling mud and determine the concentration in the formation fluid, several techniques have been used. A small amount of the drilling mud can be pumped through a mechanical agitation device known as a gas trap which is located at the surface. The purpose of the gas trap is to extract the gases from the drilling mud for measurement and analysis. Separation and quantification of the gas components, light hydrocarbon gases, is typically carried out by means of in-line gas-chromatography or gas-chromatography mass-spectrometry analysis. Gas trap sampling and analysis can be monitored continuously in real-time as part of typical mud logging activities, providing the drilling operator with real-time concentrations of the gas components per linear foot drilled for the entire depth of the well. The ability to distinguish formation fluid types, especially their gas to oil ratios (GOR), from analysis of the light gases is a highly desirable goal since time and resources spent on formation testing can be minimized. This data is essential for the economics and feasibility of any hydrocarbon reservoir.

Unfortunately, there are numerous problems associated with surface gas trap measurements. The relative concentrations of the different gas components extracted from the drilling mud and collected in the head space of the gas trap are not representative of the actual gas concentrations evolving from the drilling fluid. As a result, measured gas trap values are not representative of the gas composition of the drilling fluid or the formation fluid at depth. Additionally, uncorrected gas trap values can lead to widely divergent predictions of total fluid properties, including GOR determinations.

SUMMARY OF THE INVENTION

Aspects of embodiments of the present invention provide a method for characterizing formation fluid present in a subsurface earth formation, including, extracting a plurality of gas components from a volume of drilling mud containing formation fluid and gases, while drilling, measuring a gas trap value for each gas component of interest, determining a gas trap response factor for each gas component of interest by dividing the gas trap value by a laboratory fluid analysis value for each gas component of interest, determining a relative response factor for each gas component of interest by dividing the gas trap response factor for each gas component of interest by the gas trap response factor for the gas component of interest with the lowest molecular weight, and calculating the corrected gas trap value for each gas component of interest by dividing the gas trap value by the relative response factor for each gas component of interest, for characterizing the formation fluid from the volume of drilling mud.

In an embodiment, the method further includes a method for using previously determined relative response factors for correcting gas trap values for gas components in a drilling mud, including, correcting gas trap values for each of the gas components of interest measured in surrounding wells utilizing a similar drilling fluid.

Aspects of embodiments of the invention provide a system for performing the foregoing method. Aspects of embodiments of the invention may include a computer-readable medium encoded with computer-executable instructions for performing the foregoing method or for controlling the foregoing system. Aspects of embodiments of the invention may include a system incorporating the foregoing system and configured and arranged to provide control of the system in accordance with the foregoing method. Such a system may incorporate, for example, a computer programmed to allow a user to control the device in accordance with the method, or other methods.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
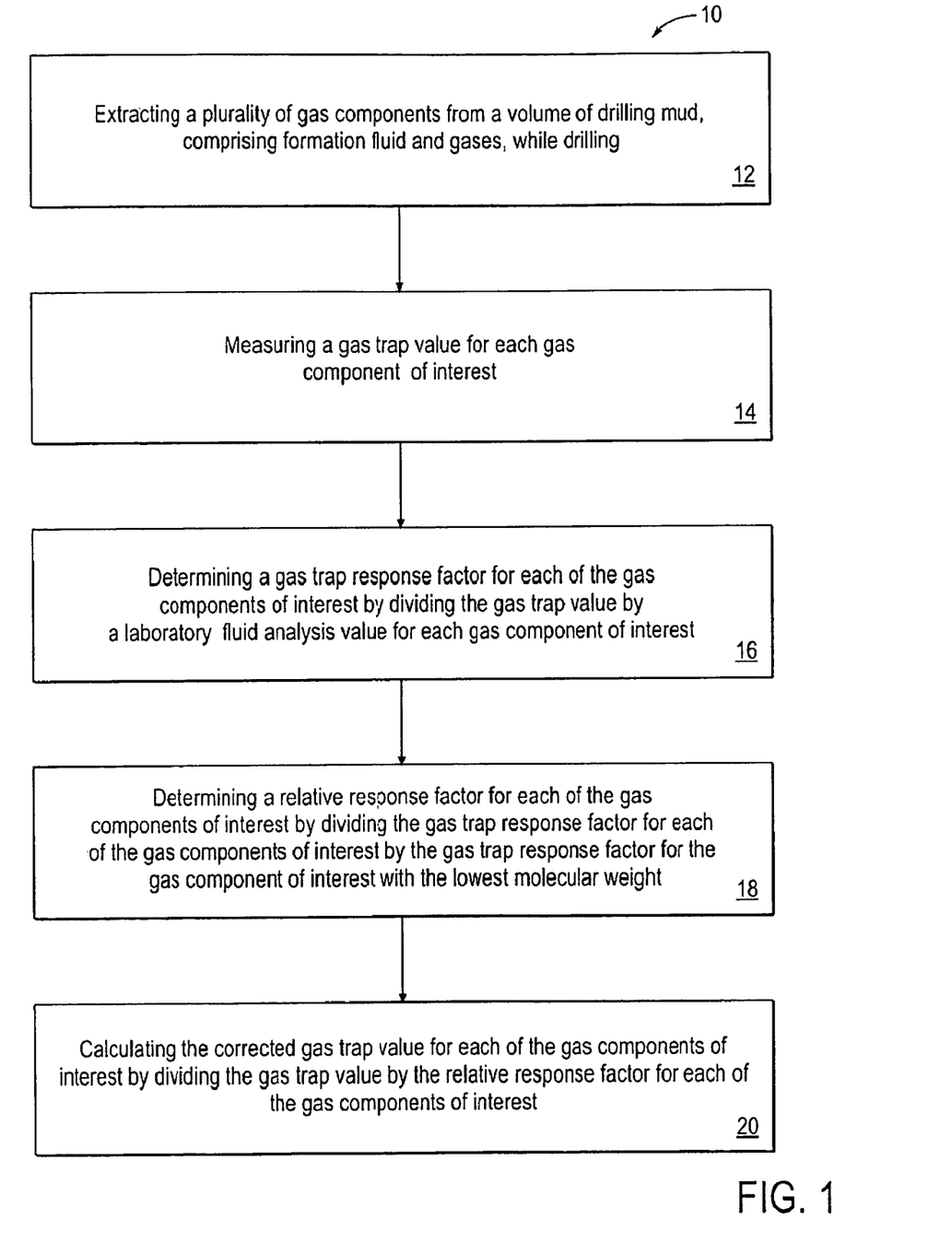
FIG. 1 is a flow chart illustrating a method in accordance with one or more embodiments of the invention.

Referring to FIG. 1, a method 10 for characterizing formation fluid present in a subsurface earth formation is shown. During drilling operations, a plurality of formation gas components are extracted 12 from a volume of circulating drilling mud which contains formation fluid and gases. In one embodiment, the formation gas components are extracted from the mud by mechanical agitation in a gas trap located at the surface. Gas trap values 14 for each gas component of interest is measured. Separation and quantification of the different formation gas components of interest, typically any of the light hydrocarbon gases (methane through pentane), is measured by means of an in-line gas-chromatograph or gas-chromatograph mass-spectrometer, and/or a total hydrocarbon analyzer. While the means for such an analysis is preferably a gas chromatograph equipped with a flame ionization detector for hydrocarbon gases, it will be appreciated that any means for analyzing the gas mixture composition could be utilized.

Figure 2:
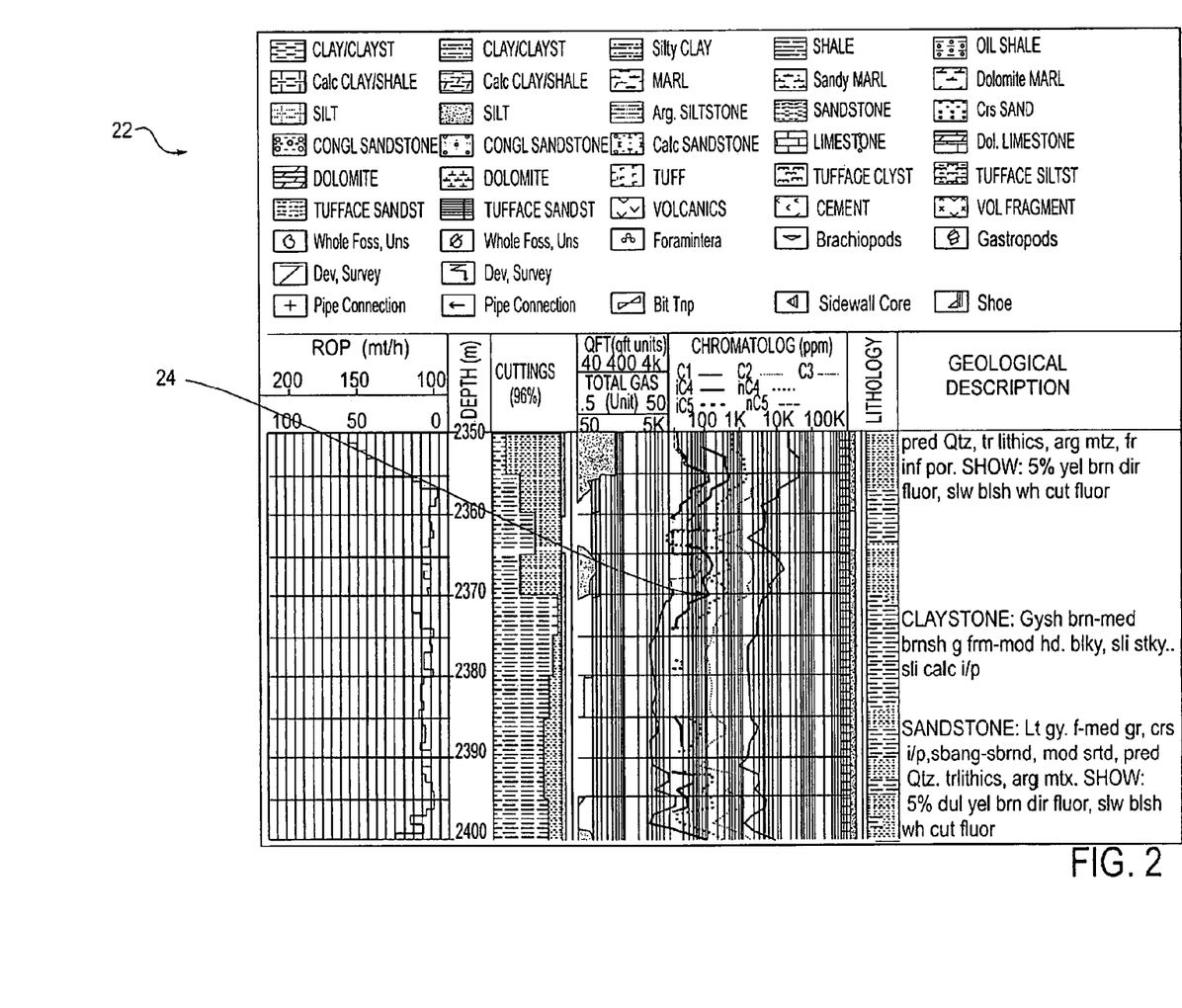
FIG. 2 is an example mudlog showing gas trap values for the formation gas components measured during drilling in accordance with one or more embodiments of the invention.

Table 1 shows correct gas trap values in accordance with an embodiment of the present invention. The concentration of each gas component in the drilling mud can be determined in parts per million (ppm) and percent of the total formation gases as shown in rows 1 and 2 in Table 1. FIG. 2 shows an example mudlog 22 including real-time continuous gas trap values 24 for the formation gas components measured during drilling.

hydrocarbon gases, it will be appreciated that any means for analyzing the gas mixture compositions could be utilized.

The laboratory fluid analysis values indicating the concentration of each gas component in the formation fluid are determined in mole % and percent of the total formation gases as shown in rows 3 and 4 in Table 1. In an embodiment, the laboratory fluid analysis values in Table 1 were established using formation fluid samples collected from a MDT run on the same well and at the same approximate depth, used to determine the gas trap values. Referring back to FIG. 1, the laboratory fluid analysis values are used to determine a gas trap response factor 16 for each gas component of interest as shown in row 5 of Table 1. The gas trap response factor can be determined by dividing the gas trap value in row 2 by the laboratory fluid analysis value in row 4 of Table 1, for each gas component of interest.

The relative concentrations of the different gas components extracted from the drilling fluid and collected in the head space of the gas trap are not representative of the actual gas concentrations evolving from the drilling fluid. This is largely due to the extraction efficiency of the different gas components. Light hydrocarbons are extracted as a function of their carbon number (volatility and solubility) i.e. methane, is extracted easier than ethane, and ethane is extracted easier than propane. In order to accurately determine the concentration of each gas component, the extraction efficiency relative to methane, or the lightest measured gas component of interest, is also needed to correct the measured gas trap response factor for each gas component.

A relative response factor is determined 18 for the gas components of interest by dividing the gas trap response

TABLE 1

| Row | | Formation Gas Component | | | | | |
| --- | --- | --- | --- | --- | --- | --- | --- |
| | | C1 | C2 | C3 | C4 | C5 | Total |
| 1 | Gas Trap Value (ppm) | 20366 | 1913 | 1039 | 593 | 314 | 24225 |
| 2 | Gas Trap Value (%) | 84.07% | 7.90% | 4.29% | 2.45% | 1.30% | 100% |
| 3 | Laboratory Fluid Analysis Value (Mole %) | 57.17 | 5.67 | 3.79 | 2.26 | 1.44 | 70.00 |
| 4 | Laboratory Fluid Analysis Value (%) | 81.29% | 8.06% | 5.39% | 3.21% | 2.05% | 100% |
| 5 | Gas Trap Response Factor (GTRF) (Gas Trap Value/LFA Value) | 1.03 | 0.98 | 0.80 | 0.76 | 0.63 | 100% |
| 6 | Relative Response Factor (RRF) (GTRF of Cx/GTRF of C1) | 1.00 | 0.95 | 0.77 | 0.74 | 0.61 | 97% |
| 7 | Corrected Gas Trap Value (ppm) (Gas Trap Value/RRF) | 20366 | 2020 | 1350 | 805 | 513 | 25054 |
| 8 | Corrected Gas Trap Value (%) (Corrected Gas Trap Value/Total) | 81.29% | 8.06% | 5.39% | 3.21% | 2.05% | 100% |

Periodic laboratory fluid analysis measurements taken directly from the formation fluid are made in order to characterize the formation fluid. This data can then be used to calibrate or correct the gas trap values. In one embodiment, the correction can consist of collecting a known volume of drilling mud at the gas trap and then distilling the sample in a steam or microwave still. The distilled gas is then measured for each gas component. In another embodiment, the calibration can consist of collecting a sample of formation fluid downhole utilizing an apparatus similar to Schlumberger Limited's Modular Formation Dynamics Tester (MDT) tool or Repeat Formation Tester (RFT) tool. Standard pressure-volume-temperature (PVT) laboratory fluid analysis can then be carried out on the formation fluid to determine the concentration of each gas component of interest in the formation fluid. While the means for such an analysis is preferably a gas chromatograph equipped with a flame ionization detector for factor for each gas component of interest by the gas trap response factor for the gas component with the lowest molecular weight. In the example provided in Table 1, the relative response factors in row 6 are calculated using the gas trap response factor of methane, typically the lowest molecular weight gas component; however, it will be appreciated that ethane could be utilized in the absence of methane and propane could be utilized in the absence of methane and ethane.

The corrected gas trap value for each of the gas components of interest is determined 20 by dividing the gas trap value in row 1 by the relative response factor in row 6 for each gas component of interest. The corrected gas trap values in row 7 and 8, are more representative of the formation fluid than the original gas trap values in rows 1 and 2 as they match the laboratory fluid analysis values in row 4. Gas trap values corrected only with laboratory fluid analysis values without correction for extraction efficiency are not as representative of the gas composition in the formation.

In another embodiment, the determined relative response factors shown in row 6 of Table 1 may be applied to the gas trap data for the rest of the well as shown in Table 2, to correct all the measured the gas trap values at all depths.

TABLE 2

| Row | | Formation Gas Component | | | | | |
|---|---|---|---|---|---|---|---|
| | | C1 | C2 | C3 | C4 | C5 | Total |
| 1 | Gas Trap Value (PPM) | 24366 | 1867 | 934 | 656 | 289 | 28112 |
| 2 | Gas Trap Value (%) | 86.67% | 6.64% | 3.32% | 2.33% | 1.03% | 100% |
| 3 | Previously Determined Relative Response Factor (RRF) (GTRF of Cx/GTRF of C1) | 1.00 | 0.95 | 0.77 | 0.74 | 0.61 | 97% |
| 4 | Corrected Gas Trap Value (PPM) (Gas Trap Value/RRF) | 24366 | 1971 | 1214 | 891 | 472 | 28914 |
| 5 | Corrected Gas Trap Value (%) (Corrected Gas Trap Value/Total) | 84.27% | 6.82% | 4.20% | 3.08% | 1.63% | 100% |

Figure 3:
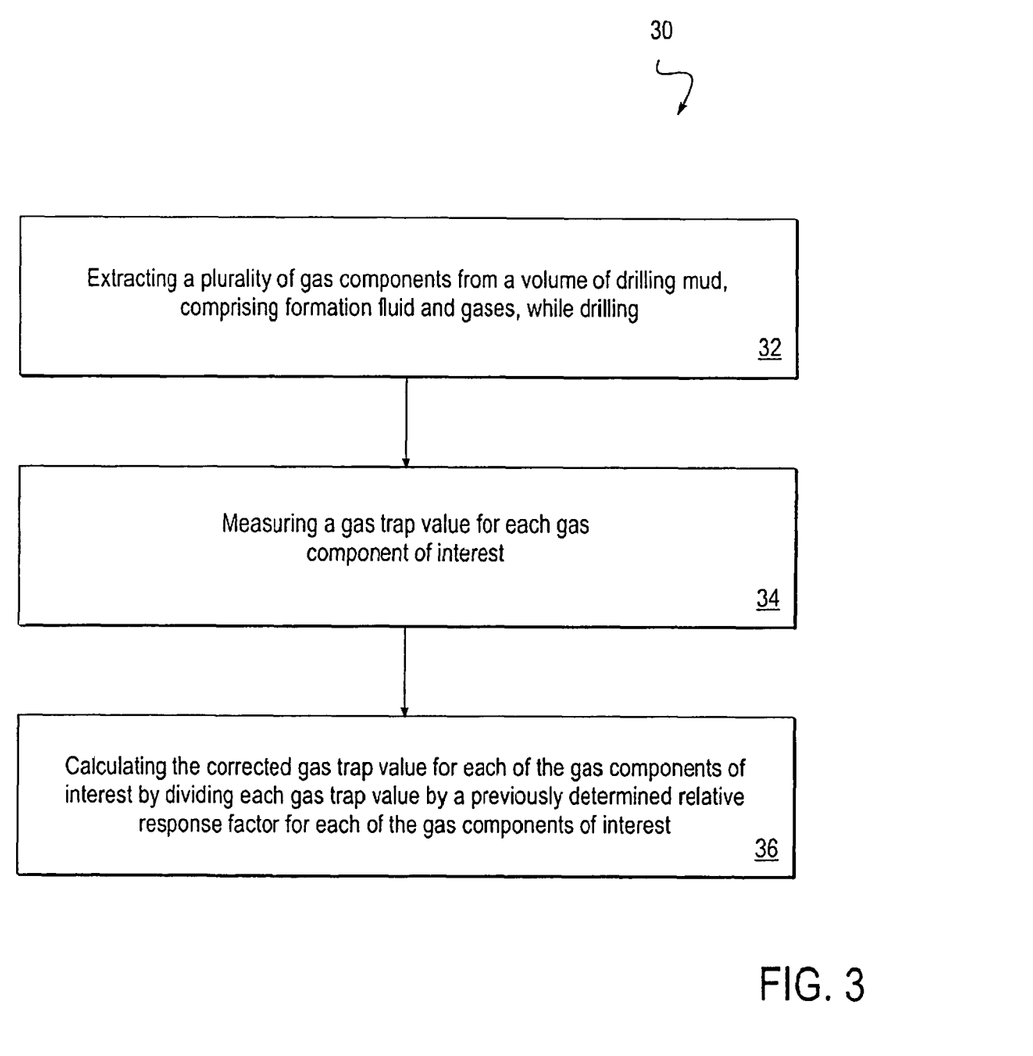
FIG. 3 is a flow chart illustrating a method in accordance with one or more embodiments of the invention.

Referring to FIG. 3, a method 30 for correcting gas trap values for gas components of interest in a drilling mud using previously determined relative response factors is shown. As in the previous example, a plurality of gas components are extracted 32 from a volume of circulating drilling mud which contains formation fluid and gases. The gas trap values are measured 34 for the gas components of interest. The corrected gas trap value for each of the gas components of interest is calculated 36 by dividing each gas trap value by a previously determined relative response factor for each gas component. The corrected gas trap values in row 5 of Table 2, is more representative of the laboratory fluid analysis values in row 4 of Table 1, than the measured uncorrected gas trap values in rows 1 and 2 of Table 2.

In an embodiment, the method utilizes available laboratory fluid analysis values to determine relative response factors for correcting gas trap values, collected during drilling, to better characterize formation fluids in zones or at depths, where laboratory fluid analysis may not be available. It will be appreciated that previously determined relative response factors can also be utilized to correct the gas trap values measured in surrounding wells using a similar drilling fluid. Gas extracts from a water-based mud easier than an oil-based mud, therefore, the relative response factors of gas components in water-based mud are significantly higher than in oil-based mud. The method is helpful for characterizing the relative response of the gas trap in more complex drilling fluid systems, such as oil-based mud systems.

The corrected gas trap values can be taken as representative of the gas composition of the formation fluid and used for predicting gas/oil ratios (GOR). The ability to distinguish formation fluid types, especially their GOR, from analysis of the formation gas components is a highly desirable goal since time and resources spent on formation testing can be minimized. As an example, GOR can be calculated as shown equation (1):

$$GOR(SCF/bbl) = 100,000 \cdot [C1+C2+C3+C4]/(\text{Rel Weight Oil}) \quad (1)$$

Where C1, C2, C3 denote methane, ethane and propane in molar concentration (% or ppm by mole); and C4 and C5 denote butane and pentane with all isomers being totaled in molar concentration (% or ppm by mole).

The relative weight of oil (Rel Weight Oil) can be calculated for methane through pentane, as shown in equation (2):

$$\text{Rel Weight Oil} = 3070 \cdot (C3 \cdot C5^2)/C4 \cdot \text{sqrt}(C2 \cdot C4) \quad (2)$$

or if pentane is not monitored, as shown in equation (3):

$$\text{Rel Weight Oil} = 1932 \cdot C4^2/\text{sqrt}(C2 \cdot C3) \quad (3)$$

Figure 4:
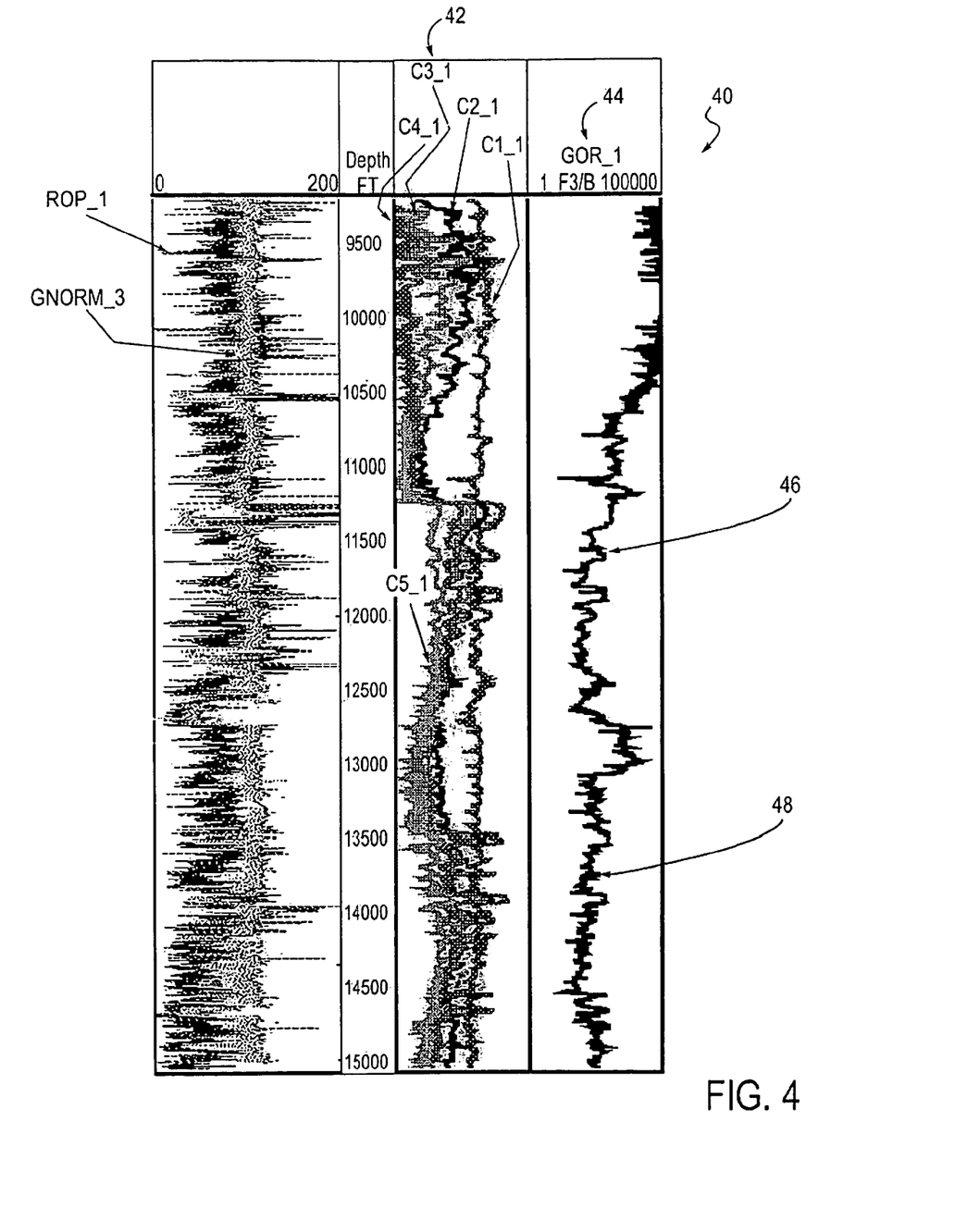
FIG. 4 is an, example mudlog showing gas trap values for the formation gas components and calculated GOR values in accordance with one or more embodiments of the invention.

FIG. 4 generally shows a method of predicting GOR using relative response factors from an adjacent well to correct gas trap values, in accordance with an embodiment of the invention. Both wells have an oil based mud system. The mud log data 40 shows the real-time monitoring of drill rate (ROP), gamma ray (GRNORM) data, depth, corrected gas trap values for methane through pentane 42, and calculated GOR. The calculated GOR values 44 were calculated using previously determined relative response factors from an adjacent well as shown in Table 3.

TABLE 3

| Row | | Formation Gas Component at Depth 11,300 ft. | | | | | |
|---|---|---|---|---|---|---|---|
| | | C1 | C2 | C3 | C4 | C5 | Total |
| 1 | Gas Trap Value (ppm) | 65259 | 2577 | 919 | 300 | 49 | 69104 |
| 2 | Gas Trap Value (%) | 94.44 | 3.78 | 1.33 | 0.43 | 0.07 | 100.00 |
| 3 | Previously Determined Relative Response Factor (RRF) from an Adjacent Well (GTRF of Cx/GTRF of C1) | 1.00 | 0.36 | 0.12 | 0.05 | 0.02 | |
| 4 | Corrected Gas Trap Value (ppm) (Gas Trap Value/RRF) | 65259 | 7078 | 7916 | 5769 | 3267 | 89288 |
| 5 | Corrected Gas Trap Value (%) (Corrected Gas Trap Value/Total) | 73.09 | 7.93 | 8.87 | 6.46 | 3.66 | 100 |

Using the measured uncorrected gas trap values for each gas component in row 1 of Table 3 in equations (1)-(3) the calculated GOR values are:

GOR for $C1-C5 = 269089$ SCF/bbl

GOR for $C1-C4 = 61160$ SCF/bbl

Using the corrected gas tap values for each gas component in row 4 of Table 3 in equations (1)-(3) the calculated GOR values are:

GOR for $C1$-$C5$=1269 SCF/bbl

GOR for $C1$-$C4$=1039 SCF/bbl

The calculated GOR 44 using the corrected gas trap values closely matched the reported GOR of 1136 SCF/bbl calculated directly from the laboratory fluid analysis values, as shown at depth 46 in FIG. 4. Likewise, the calculated GOR using the corrected gas trap values was 720 scfs/bbl which closely matched the reported GOR of 750 SCF/bbl calculated directly from the laboratory fluid analysis values, as shown at depth 48. As illustrated, uncorrected gas trap values are not representative of the actual gas concentrations evolving from the drilling fluid and can lead to widely divergent predictions of formation fluid properties, including GOR determinations. Accurate predictions of formation fluid properties and GOR determinations can be made using relative response factors to correct the gas trap values for gas components in a drilling mud.

Figure 5:
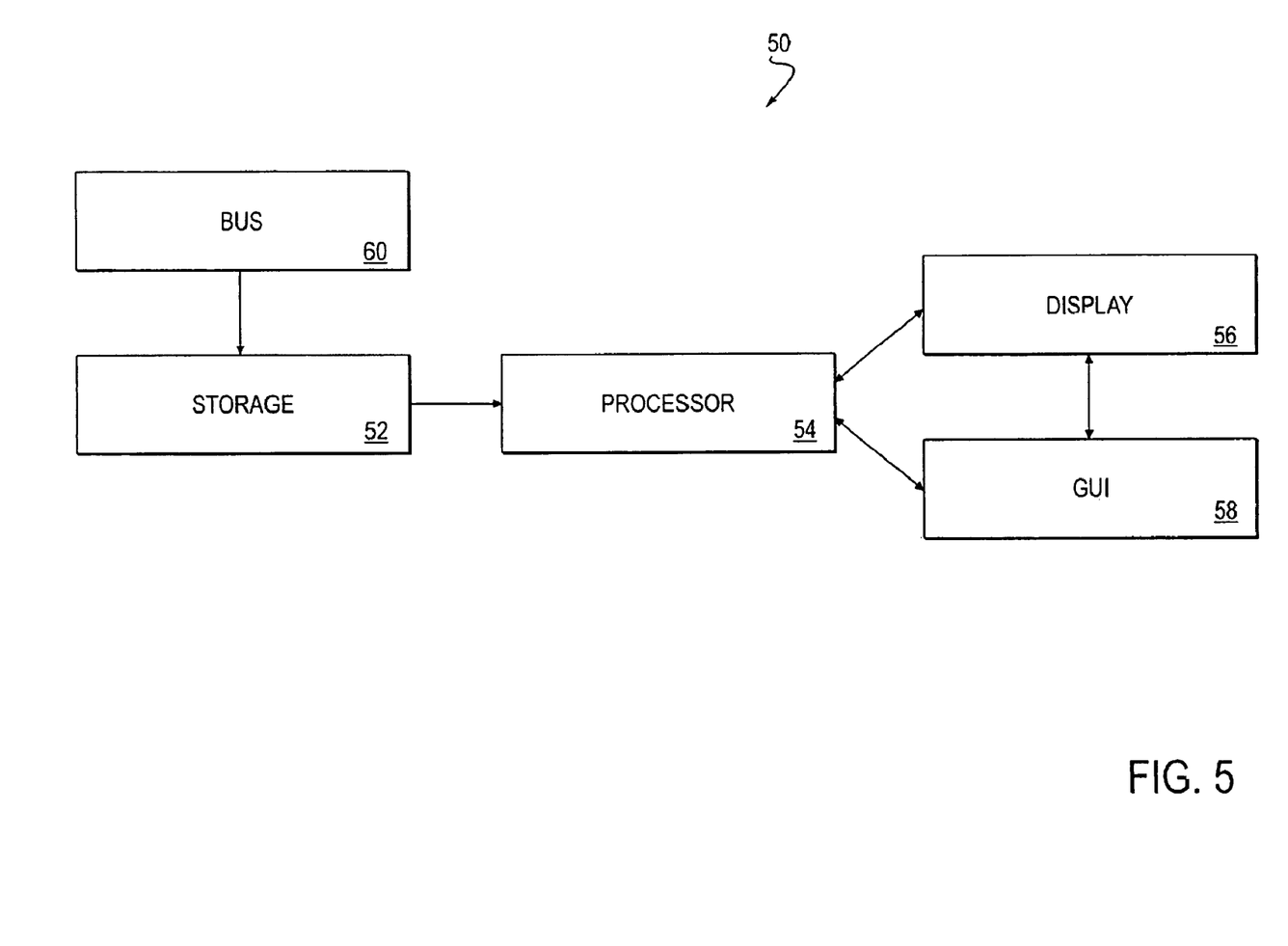
FIG. 5 is a schematic illustration of an embodiment of a system for performing methods in accordance with one or more embodiments of the invention.

A system for performing the method is schematically illustrated in FIG. 5. A system 50 includes a data storage device or memory 52. The stored data may be made available to a processor 54, such as a programmable general purpose computer. The processor 54 may include interface components such as a display 56 and a graphical user interface 58. The graphical user interface (GUI) may be used both to display data and processed data products and to allow the user to select among options for implementing aspects of the method. Data may be transferred to the system 50 via a bus 60 either directly from a data acquisition device, or from an intermediate storage or processing facility (not shown).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, though reference is made herein to a computer, this may include a general purpose computer, a purpose-built computer, an ASIC programmed to execute the methods, a computer array or network, or other appropriate computing device. As a further example, it is to be understood that the present invention contemplates that, to the extent possible, one or more features of any embodiment can be combined with one or more features of any other embodiment.

What is claimed is:

1. A method for characterizing formation fluid present in a subsurface earth formation, the method comprising:
   extracting a plurality of gas components from a volume of drilling mud comprising formation fluid and gases, while drilling;
   measuring a gas trap value for each gas component of interest;
   determining a gas trap response factor for each gas component of interest by dividing the gas trap value by a laboratory fluid analysis value for each gas component of interest;
   determining a relative response factor for each gas component of interest by dividing the gas trap response factor for each gas component of interest by the gas trap response factor for the gas component of interest with the lowest molecular weight; and
   calculating the corrected gas trap value for each gas component of interest by dividing the gas trap value by the relative response factor for each gas component of interest;
   wherein the corrected gas trap value for each gas component of interest is utilized to calculate gas/oil ratios for characterizing the formation fluid from the volume of drilling mud.

2. A method in accordance with claim 1, wherein the plurality of gas components are extracted from the volume of drilling mud using a gas trap.

3. A method in accordance with claim 1, wherein the plurality of gas components comprises methane, ethane, propane, butane, and/or pentane.

4. A method in accordance with claim 1, wherein the gas components of interest are chosen from the group of methane, ethane, propane, butane, and/or pentane.

5. A method in accordance with claim 1, wherein the gas trap values are measured using gas chromatography or gas chromatography-mass spectrometry.

6. A method in accordance with claim 1, wherein the laboratory fluid analysis value is measured using gas chromatography or gas chromatography-mass spectrometry.

7. A method in accordance with claim 1, wherein the corrected gas trap values are used to calculate gas to oil ratios to characterize the formation fluid.

8. A method in accordance with claim 1, wherein the determined relative response factors are utilized to correct gas trap values measured in the same well at various depths.

9. A method in accordance with claim 1, wherein the determined relative response factors are utilized to correct gas trap values measured in surrounding wells utilizing a similar drilling fluid.

10. A method for using previously determined relative response factors for correcting gas trap values for gas components in a drilling mud, comprising:
    extracting a plurality of gas components from a volume of drilling mud comprising formation fluid and gases, while drilling;
    measuring a gas trap value for each gas components of interest; and
    calculating the corrected gas trap value for each of the gas components of interest by dividing each gas trap value by a previously determined relative response factor for each of the gas components of interest;
    wherein, the corrected gas trap value for each of the gas components of interest is utilized to calculate gas/oil ratios for characterizing formation fluids from the volume of drilling mud.

11. The method in accordance with claim 10, wherein the previously determined relative response factor for each gas component of interest is utilized to correct gas trap values for each of the gas components of interest measured in surrounding wells utilizing a similar drilling fluid.

12. A system for automatically correcting a plurality of gas trap values, comprising:
    a data storage device having non-transitory computer readable data including mud logging data relating to the plurality gas trap values;
    a processor, configured and arranged to execute machine executable instructions stored in a processor accessible memory for performing a method comprising:
        acquiring a gas trap value for each gas component of interest;

determining a gas trap response factor for each gas component of interest by dividing the gas trap value by a laboratory fluid analysis value for each gas component of interest;

determining a relative response factor for each gas component of interest by dividing the gas trap response factor for each gas component of interest by the gas trap response factor for the gas component of interest with the lowest molecular weight;

correcting the gas trap value for each gas component of interest by dividing the gas trap value by the relative response factor for each gas component of interest; and utilizing the corrected gas trap value for each gas component of interest to calculate gas/oil ratios for characterizing formation fluids.

13. A system as in claim 12, further comprising a user interface configured and arranged to allow a user to adjust parameters used in correcting the gas trap value for each gas component of interest.

14. A system as in claim 12, further comprising a user interface configured and arranged to allow a user to adjust parameters used in the calculation gas/oil ratios.

15. A system as in claim 12, further comprising a display, configured and arranged to display a layer structure of a subsurface region from which the formation fluid and gases were taken, based, at least in part, on the gas trap values.

* * * * *